United States Patent
Toreki et al.

(10) Patent No.: US 8,088,400 B2
(45) Date of Patent: Jan. 3, 2012

(54) DISINFECTANT WITH QUARTERNARY AMMONIUM POLYMER AND COPOLYMERS

(75) Inventors: William Toreki, Gainesville, FL (US); Gerald Olderman, Bedford, MA (US)

(73) Assignee: Quick-Med Technologies, Inc., Gainesville, FL (US)

( * ) Notice: Subject to any disclaimer, the term of this patent is extended or adjusted under 35 U.S.C. 154(b) by 601 days.

(21) Appl. No.: 12/064,487

(22) PCT Filed: Aug. 22, 2006

(86) PCT No.: PCT/US2006/032954
§ 371 (c)(1),
(2), (4) Date: Nov. 18, 2008

(87) PCT Pub. No.: WO2007/024973
PCT Pub. Date: Mar. 1, 2007

(65) Prior Publication Data
US 2009/0246165 A1    Oct. 1, 2009

Related U.S. Application Data

(60) Provisional application No. 60/710,128, filed on Aug. 22, 2005, provisional application No. 60/806,196, filed on Jun. 29, 2006.

(51) Int. Cl.
| | |
|---|---|
| *A01N 25/00* | (2006.01) |
| *C09D 5/16* | (2006.01) |
| *C08G 79/00* | (2006.01) |
| *C08G 63/00* | (2006.01) |
| *C08L 71/12* | (2006.01) |
| *C08F 283/04* | (2006.01) |
| *C08F 283/02* | (2006.01) |
| *A61K 31/74* | (2006.01) |
| *A61K 31/765* | (2006.01) |

(52) U.S. Cl. ............... 424/405; 106/18.21; 106/18.32; 525/390; 525/437; 525/453; 525/467; 525/523; 424/78.02; 424/78.03; 424/78.37

(58) Field of Classification Search ................... 424/405
See application file for complete search history.

(56) References Cited

U.S. PATENT DOCUMENTS

| | | | | |
|---|---|---|---|---|
| 4,110,286 A | * | 8/1978 | Vandegaer et al. | ........... 524/874 |
| 4,789,720 A | | 12/1988 | Teffenhart | |
| 5,084,096 A | * | 1/1992 | Stovicek | ........... 106/18.21 |
| 6,017,561 A | * | 1/2000 | Zhou et al. | ............ 424/486 |
| 6,605,666 B1 | | 8/2003 | Scholz et al. | |
| 2003/0091641 A1 | * | 5/2003 | Tiller et al. | ............ 424/486 |
| 2006/0051385 A1 | | 3/2006 | Scholz | |
| 2009/0042870 A1 | | 2/2009 | Fellows et al. | |

FOREIGN PATENT DOCUMENTS

| | | |
|---|---|---|
| JP | 2006-213708 A | 8/2006 |
| WO | 2007024973 A1 | 3/2007 |

\* cited by examiner

*Primary Examiner* — Richard Schnizer
*Assistant Examiner* — Audrea Buckley
(74) *Attorney, Agent, or Firm* — Gerry J. Elman; Elman Technology Law, P.C.

(57) ABSTRACT

An alcohol-soluble, water-insoluble, disinfectant composition and a method of using the same for disinfecting and for providing a prolonged antimicrobial property to a variety of surfaces, including skin. The composition comprises an antimicrobial polymer that is capable of imparting an antimicrobial property to a surface without the use of a metal or metal-containing compound. The composition is applied to a surface and allowed to evaporate leaving a coating of antimicrobial polymer.

14 Claims, No Drawings

DISINFECTANT WITH QUARTERNARY AMMONIUM POLYMER AND COPOLYMERS

CROSS-REFERENCE TO RELATED APPLICATIONS

Applicants hereby claim the benefit of U.S. Provisional Patent Application 60/710,128, filed Aug. 22, 2005, and U.S. Provisional Patent Application 60/806,196, filed Jun. 29, 2006; and international patent application PCT/US2006/032954, filed Aug. 22, 2006. The entire contents of the aforementioned patent applications are hereby incorporated by reference.

TECHNICAL FIELD

This invention relates to disinfectants for surfaces, including skin, that provide sustained antimicrobial activity for prolonged periods following their application to the surface.

BACKGROUND ART

Human and animal health can be adversely affected by many microorganisms, including bacteria, yeasts, viruses, fungi, mold, and protozoa. Human and animal contact with microorganisms is known to cause a wide variety of diseases, illnesses, and ailments.

It is well known that the washing of hard surfaces (e.g. food preparation surfaces and surgical room equipment), food (e.g. fruits and vegetables), and skin (e.g. hands) with soap and water, can remove many microorganisms from those surfaces. Removal of microorganisms by hand washing with soap is largely due to a combination of the surfactancy of the soap and the mechanical action of the washing procedure. Because washing with soap is effective at removing a substantial number of microorganisms already present, but has only a minimal, if any, lasting or persistent effect on microorganisms that subsequently come into contact with the already washed hands, it is often recommended that people wash their hands frequently in order to reduce the spread of viruses, bacteria, and other microorganisms. Compliance with this recommendation is important for an individual's personal health and hygiene, but is especially important for individuals working in the health and food industries.

Antimicrobial cleansing products for the removal of microorganisms from surfaces, including skin, are available in a variety of types. The most common types utilized for personal hygiene and by personnel working in the health and food industries, include those containing soaps and those containing alcohol.

Traditional rinse-off disinfectant products, such as detergents and soaps, are generally effective at reducing the number of microorganisms present on a surface when proper procedures are employed. For example, Dial® liquid soaps containing triclosan, when used for hand washing, have been shown to reduce the number of bacteria present on the skin by about 2.0-2.5 orders of magnitude (99.0-99.7%) after one 30-second handwash, as measured by standard Health Care Personal Handwash Tests (HCPHWT). In other words, after washing, the washed skin is contaminated with only 0.3%-1.0% of the number of bacteria than was the unwashed skin before the 30-second handwash. Although, when used properly, soaps are capable of removing the majority of bacteria that are present, the persistence of any antimicrobial activity remaining on the surface is minimal, so immediately following hand washing, re-contamination of the hands begins to occur through contact with other contaminated surfaces. In addition, because these traditional rinse-off disinfectant products were developed for use in a washing procedure that uses a substantial amount of water; their use is limited to locations where a substantial amount of water is available.

Another commonly used type of disinfectant are those products containing relatively high levels of alcohol. Alcohol-based disinfectants result in the immediate removal or inactivation of a substantial portion of microorganisms present on the treated surface. Disinfectants based on alcohol, typically ethanol, have an additional advantage as disinfectants because alcohol readily evaporates from the skin at body temperature. Purell® is one example of a skin disinfectant that uses alcohol as the active ingredient. Again, although properly applied alcohol-based disinfectants are generally effective at removing or destroying bacteria that are present on the skin prior to application, immediately following treatment, re-contamination of treated skin begins to occur through contact with other contaminated surfaces.

Recent studies indicate that alcohol-based sanitizers with less than approximately 60% alcohol content may not be suitable to provide a desirable degree of antimicrobial activity, and alcohol contents above 95% are also less potent because proteins are not denatured easily in the absence of water ["*Hand Hygiene Revisited: Another Look at Hand Sanitizers and Antibacterial Soap*" SAFEFOOD NEWS—Spring 2004—Vol 8 No. 3, Colorado State University Cooperative Extension].

Other water-soluble active ingredients have been used in skin disinfectants, instead of, or in combination with, alcohol. Birnbaum et al., (U.S. Pat. No. 6,441,045) disclose a water-soluble quaternary compound for use as a skin disinfectant. Beerse et al., (U.S. Pat. No. 6,217,887) disclose an antimicrobial composition for skin that is meant to be left-on rather than rinsed-off, which contains an antimicrobial active, an anionic surfactant, a proton-donating agent, in a solution containing up to 98.85% water. Petersen et al., (U.S. Pat. No. 6,627,207) disclose a water-based, quick-drying, gel-type disinfecting composition having a low alcohol content (<30%). Osborne et al., (U.S. Pat. Nos. 5,776,430 and 5,906,808) describe a topical antimicrobial cleanser composition containing 0.65-0.85% chlorhexidine gluconate, or a pharmaceutically acceptable salt, and 50-60% denatured alcohol. Kross (U.S. Pat. No. 5,597,561) discloses water-based, adherent disinfecting composition directed at the prevention of microbial infections, which contains protic acid, a metal chlorite, and a gelling agent. Smyth et al., (U.S. Pat. No. 5,916,568) disclose a quick-drying hand sanitizer composed of alcohol, hydrogen peroxide, and an emollient to help prevent skin irritation. Sawan et al., (U.S. Pat. No. 6,180,584) disclose a disinfectant composition comprised of a polymeric, film-forming material and a metallic biocide in a carrier, which, when applied to a surface, forms a water-insoluble polymeric film on the surface in which the biocide is non-leachably bound to, complexed with, associated with, or dispersed.

Causton et al., (U.S. Pat. No. 5,869,600) disclose the use of water-insoluble, alcohol-soluble copolymers containing some level of quaternary ammonium groups for use as film-forming polymers utilized as antiperspirants.

Other approaches have employed methods that attach reactive silane-based quaternary ammonium compounds to particular substrates via a siloxane bond. For example, AEGIS Environments' product line includes products that utilize polymers of 3-(trimethoxysilyl)propyldimethyloctadecyl ammonium chloride, and are generally applied using alcohol-based solutions. According to product literature, AEM 5700 is 43% 3-(trimethoxysilyl) propyldimethyloctadecyl ammonium chloride in methanol, which can be used to coat the surface of textiles and other objects. This method results in the formation of a permanent covalent bond between the quaternary ammonium antimicrobial compound and the surface being treated. Removal of the applied antimicrobial is thus nearly impossible, even using alcohol-based solvents. Furthermore, the reactive trimethoxysilyl compounds are toxic and not suitable for use on skin.

Sawan (U.S. Pat. No. 6,264,936) describes an antimicrobial material which can be used to form on the surface of a substrate an antimicrobial coating or layer which kills microorganisms on contact. The antimicrobial coating or layer, characterized in the reference as "non-leaching," is a combination of an organic matrix immobilized on the surface of the substrate to having biocidal metallic materials associated with the matrix. When a microorganism contacts the coating or layer, the biocidal metallic material is transferred to the microorganism in amounts sufficient to kill it. Specifically, the metallic antimicrobial agent used is silver. Although this method purports to provide a "non-leachable" coating, the mere fact that the metallic antimicrobial agent "is transferred" to the microorganism is contrary to the common definition of non-leachable. Furthermore, it is known that although silver and silver salts have very low solubility, the mechanism of antimicrobial activity is dependent on a finite solution concentration of silver ions. Indeed, Sawan later (column 3, line 9) qualifies the above statement to read "substantially low leachables". In a preferred embodiment of Sawan's patent, the organic material comprises a polyhexamethylene biguanide polymer which is crosslinked with an epoxide, such as N,N-bismethylene diglycidylaniline, to form a crosslinked network or matrix. This crosslinking step is necessary to prevent dissolution of the matrix. The materials described by Sawan generally require a curing step, generally in the range of 80° to 120° C., which is unsuitable for many substrates, particularly human skin. Furthermore, the preferred organic matrix polymer (polyhexamethylene biguanide) is known to be toxic to human cells in high concentrations (see U.S. Pat. No. 6,369,289 B1). The use of silver as an antimicrobial agent also incurs some undesirable effects. One disadvantage to this approach is that certain bacteria have been able to develop resistance to silver. (Silver S., "*Bacterial silver resistance: molecular biology and uses and misuses of silver compounds.*" FEMS Microbiology Reviews, 2003; 27:341-353). Another disadvantage to this approach is that diffusing silver may be able to enter the wound and may potentially stain the skin. An additional disadvantage of silver is the high cost of the raw material. Similar approaches are described in U.S. Pat. Nos. 6,180,584; 6,126,931; 6,030632; 5,869,073, 5,849,311; and 5,817,325.

There is a need for improved means and methods for disinfecting surfaces, not only for improved personal hygiene, but also to reduce potential sources of contamination in both health and food industries. With currently used non-persistent disinfectants, personnel in the health industry (e.g. doctors, nurses, and patients) and the food industry (e.g. food handlers, food preparers, cooks, and servers) must apply a disinfectant, such as soap, to their skin several, and sometimes 20 or more times, a day. Consequently, there exists a need, for personal hygiene and hygiene within the health and food industries, for a disinfectant that can effectively sanitize a surface and persist actively on that surface to combat microorganisms that subsequently come into contact with the treated surface.

DISCLOSURE OF THE INVENTION

Industrial Applicability

The need for an effective, persistent surface disinfectant is felt in all aspects of the health industry. It is an aspect of the current invention that the invention would be useful to disinfect skin prior to surgery, injection, phlebotomy, and catheter insertion. Microorganisms present a threat to the health and safety of patients whenever the skin is penetrated, broken, or breached. For example, such pathogens may be a hazard during surgical procedures. Without adequate disinfection of the incision site prior to surgery, microorganisms present on the skin gain access to the incision during or following surgery and cause infection. To prevent such infections, it is critical to disinfect the incision site prior to surgery with a disinfectant that possesses a high antimicrobial activity and a broad spectrum of action. Since surgical procedures can last for many hours, it is also important that the initial disinfection of the incision site persists and provides sustained antimicrobial activity for an extended period of time. In the United States, the Food and Drug Administration requires that a pre-surgical skin disinfectant be capable of reducing the number of flora on dry skin areas, such as an abdomen, by at least 2.5 orders of magnitude or to levels that are too low for reliable quantification (less than about 25 cfu/cm$^2$). On moist skin, such as inguinal areas, the disinfectant must reduce the initial bacterial population by a minimum of 3.2 logs (1.5× 10$^3$ cfu/mL) and be able to maintain this level for at least four hours.

The need for an effective, persistent, and durable surface disinfectant is also felt in all aspects of the food industry, including food collection (e.g. sanitation of cow teats), food processing (e.g. slaughterhouses), food packaging (e.g. fish canneries), and food distribution (e.g. restaurants and food stores). It is an aspect of the current invention that the composition would be useful wherever a person has food handling responsibilities and particularly useful wherever proper hygiene is made difficult because the same individual has both food handling and money handling responsibilities (e.g. deli shop cashiers and wait staff).

The ability of many organisms to develop resistance to antimicrobial compounds is a serious problem. Reports of rampant infections from organisms such as methacillin-resistant *Staph. aureus* (MSRA) abound in the news media. Such resistance is known to occur for many antibiotics, as well as for metal-based systems (such as silver). Quaternary ammonium compounds, on the other hand, do not promote development of resistant organisms.

Definitions

As used herein, the following terms have the following meanings:

"Microbe" or "microorganism" refers to any organism or combination of organisms such as bacteria, viruses, protozoa, yeasts, fingi, molds, or spores formed by any of these.

"Antimicrobial" refers to the microbicidal or microbistatic properties of a compound, composition, article, or material that enables it to kill, destroy, inactivate, or neutralize a microorganism; or to prevent or reduce the growth, ability to survive, or propagation of a microorganism.

A "disinfectant" is an agent that destroys, neutralizes, or otherwise interferes with the growth or survival of microorganisms.

"Alcohol" means a volatile liquid having the formula $C_nH_{2n+1}OH$ where n is from 1 to 4.

"Soluble" means that the substance is capable of being dissolved in a quantity of a specified liquid, such as alcohol or water.

"Readily soluble" means that the solute in question is virtually 100% soluble, capable of forming a solution at room temperature containing up to 20 wt % of the solute, in a specified solvent, e.g. a particular alcohol.

"Insoluble" means that the substance will not significantly dissolve in a large excess (e.g. >100-fold) of a particular solvent, e.g. water.

"Volatile" means that the solvent or liquid fully evaporates at room temperature.

"Durable" means insoluble in water, not easily removed by, for example, perspiration, incidental contact with aqueous fluids, or light washing with aqueous fluids.

"Contact-killing" means a means of destroying which does not require leaching, elution, or releasing into contacting fluids at levels that would result in fluid disinfection.

"Antimicrobial metallic material" means a metal, such as colloidal silver, or a metal salt, in a form capable of imparting antimicrobial activity to a composition. This invention provides antimicrobial activity in the absence of an antimicrobial metallic material.

The current invention provides a disinfectant composition comprising an alcohol-soluble, water-insoluble, antimicrobial polymer suitable for disinfecting and for providing a prolonged antimicrobial property to a variety of surfaces, including skin.

The invention provides a disinfectant composition, comprising an antimicrobial polymer in an alcohol-containing solvent, wherein the antimicrobial polymer is readily soluble in alcohol, but insoluble in water, and wherein the solvent serves as a carrier for applying said antimicrobial polymer to a surface, whereby said surface acquires a coating of the antimicrobial polymer.

It is an advantage of the invention that the antimicrobial polymer imparts a lasting antimicrobial activity to said surface.

It is an aspect of the invention that the antimicrobial polymer is selected so that its antimicrobial activity occurs by virtue of a contact-killing mechanism, which does not require leaching, elution, or releasing into contacting fluids at levels that would result in fluid disinfection. Moreover it is preferred that the antimicrobial polymer does not appreciably leach, elute or release from the surface to which the antimicrobial composition is applied.

In particular embodiments of the invention the alcohol-containing solvent contains at least one alcohol selected from the group consisting of ethanol, methanol, and isopropanol.

In particular embodiments of this invention the alcohol content of the disinfectant solution is between 60% and 95% by weight.

In particular embodiments of the invention the antimicrobial polymer may consist essentially of molecules that are comprised of at least one allyl- or vinyl-containing monomeric moiety. In some embodiments of the invention the antimicrobial polymer consists essentially of molecules that are comprised of at least one quaternary-ammonium-containing monomeric moiety.

It is an aspect of this invention that quaternary ammonium moieties are covalently bonded to the polymer, or attached to the molecular structure of the antimicrobial polymer by covalent chemical bonds, and are part of the polymer molecular structure, and that said quaternary ammonium moieties are located either in the main-chain of the polymer, or in side-groups of the polymer. "Main-chain" and "side-groups" are terms commonly used to describe polymer molecular structure and will be familiar to one skilled in the art.

Some of the antimicrobial polymeric molecules used in the present invention can be synthesized by step-growth polymerization, such as by the reaction of a difunctional alcohol with a diisocyanate to form a polyurethane polymer that contains at least one quaternary ammonium group in a monomeric moiety which is attached to the molecular structure of the polymer by covalent chemical bonding. Preferably, the number of quaternary ammonium groups in the polyurethane polymer will be at least one mole ($6.02 \times 10^{23}$) per 650 grams of polyurethane polymer. More preferably, the number of quaternary ammonium groups in the polyurethane polymer will be at least one mole ($6.02 \times 10^{23}$) per 350 grams of polyurethane polymer.

The antimicrobial polymeric molecules may have an average degree of polymerization of 5 to 25,000; preferably 50 to 10,000; and more preferably 100 to 5,000.

In one aspect of the invention, the disinfectant composition is applied to a surface, which surface may be the skin of an animal, the skin of a human, a nonliving porous surface, or a nonliving nonporous surface.

For example, the disinfectant composition may be applied to skin before a medical procedure. The term "medical procedure" includes, without limitation, surgery, injection, phlebotomy, and catheter insertion, and further includes other procedures that breach the skin.

In another aspect of the invention, the disinfectant composition may be applied to the hands of health care workers to minimize transmission of microbes between infected patients or between infected sites on a patient.

An advantage of the invention is that many embodiments of antimicrobial polymer coating do not visibly stain the skin, and are colorless.

Another aspect of the invention provides a disinfectant composition that contains a dye, enabling the coating to be visualized. In some embodiments, the dye is bonded to the antimicrobial polymer, thereby preventing migration of the dye from the coating.

An advantage of the invention is that, after the solvent has evaporated, the coating is generally odorless.

Many embodiments of the disinfectant composition have a pH between approximately 5 and approximately 9, preferably between 6.5 and 8.0.

Various embodiments of the disinfectant composition may be applied to the skin in a form selected from the group consisting of liquid, gel, foam, and aerosol.

Optionally, the disinfectant composition additionally contains at least one additive selected from the group consisting of a drug, an antimicrobial, an antiseptic, a thickening agent, a moisturizer, an emollient, a vitamin, a temporary dye, a permanent dye, and a UV absorber. When such an additive is an antimicrobial, it may be an alcohol, which also serves as a solvent for the antimicrobial polymer with persistent activity. The antimicrobial or antiseptic additive may also be a quaternary ammonium salt, a biguanide, or a phenolic compound. In a particular embodiment the added antimicrobial or antiseptic is a quaternary ammonium salt, such as benzalkonium chloride, benzethonium chloride, dimethyldidecyl ammonium chloride, or mixtures thereof. In another embodiment the added antimicrobial or antiseptic is a biguanide, such as chlorhexidine or poly(hexamethylene biguanide). In another embodiment, the added antimicrobial or antiseptic is a phenolic compound, such as phenol or triclosan. In some embodiments, the emollient is propylene glycol, dipropylene glycol, glycerol, or mixtures thereof. In another embodiment, the drug is an antibiotic, anti-inflammatory, an analgesic, or an anesthetic agent.

In some embodiments, the antimicrobial polymer can be manufactured by mixing one species of monomer with at least one other different species of monomer, and copolymerizing the monomers, wherein at least one of the monomers bears at least one quaternary ammonium moiety, producing a copolymer that is readily soluble in alcohol and insoluble in water.

In some embodiments the antimicrobial polymer can be manufactured by polymerizing a monomer, wherein the monomer bears at least one quaternary ammonium moiety, producing a polymer that is readily soluble in alcohol and insoluble in water.

In another optional aspect of the invention, a polymer is provided which contains both dye (e.g. fluorescein) and antimicrobial (e.g. quaternary ammonium) units both covalently bonded to the polymer molecular structure, or attached to the polymer molecular structure by covalent chemical bonds, and hence are part of the polymer molecular structure, and are located either in the main-chain of the polymer, or in sidegroups of the polymer.

It is an aspect of this invention to provide a polyurethane polymer which is readily soluble in a solvent consisting essentially of alcohol, but insoluble in water, and which contains at least one quaternary ammonium moiety attached to the molecular structure of the polymer by covalent chemical bonds, and which is capable of providing durable antimicrobial activity when applied to a surface.

It is an aspect of this invention that there is no covalent chemical bond formed between the antimicrobial polymer and the substrate to which it is applied. Furthermore, the antimicrobial polymer may be removed from a substrate to which it has been applied by using alcohol or a solvent having significant alcohol content.

It is an aspect of this invention that metals or metallic salts are not used as antimicrobial agents.

It is an aspect of this invention that a curing step is not required to impart insolubility to the antimicrobial polymer after it has been applied to a surface.

DETAILED DESCRIPTION

One exemplary embodiment of the current invention utilizes an antimicrobial polymer having polymeric molecules that are composed of one type of monomeric moiety; alternatively, the polymeric molecules may be composed of more than one type of monomeric moiety. In exemplary embodiments of the current invention, quaternary ammonium moieties impart antimicrobial activity to the polymeric molecules. Desirably such quaternary ammonium-containing monomeric moieties constitute at least 2% by weight of the polymeric molecules, more preferably at least 10% of the polymeric molecules, and most preferably at least 25% of the polymeric molecules. Preferably, the number of quaternary ammonium moieties in the antimicrobial polymer will be at least one mole ($6.02 \times 10^{23}$) per 650 grams of polymer. More preferably, the number of quaternary ammonium moieties in the antimicrobial polymer will be at least one mole ($6.02 \times 10^{23}$) per 350 grams of polymer.

The antimicrobial polymer is formulated to be insoluble in water and readily soluble in aqueous solutions of at least 75 wt % alcohol. More preferably it is formulated to be insoluble in water and is readily soluble in such solutions of at least 50 wt % alcohol, and most preferably it is formulated to be insoluble in water and readily soluble in solutions of at least 25 wt % alcohol. It is an aspect of the current invention that the antimicrobial polymer can be applied to surfaces, including skin, dissolved in an alcohol-containing solvent.

The relative solubility of polymers in different solvents is not trivial. This invention pertains to polymers that are soluble in alcohol, yet insoluble in water. This specific combination of properties is manifested in only a relatively small number of the many different types of known natural and synthetic polymers. Polymers may generally be divided into two groups: water-soluble, and water-insoluble. Some water-insoluble polymers may be soluble in various organic solvents. Solubility generally depends on the properties of the particular polymer-solvent combination, with soluble combinations resulting when the chemical structures of the polymer and solvent are similar. Polarity of the solvent is perhaps the most important consideration. Polarity of some common solvents in order of most polar to least polar are: water, ethanol, ether, toluene, and hexane. Many water-soluble polymers are also soluble in alcohol. Among the alcohols, the polarity decreases in the order of methanol, ethanol, and isopropanol, with the polarity of methanol being closest to that of water. Thus, many water-soluble polymers are more soluble in methanol, than in ethanol or isopropanol. Ethanol and isopropanol are preferred solvents for the practice of this invention. Isopropanol is not generally a very good solvent for most polymers. Even polyethylene oxide, which is highly soluble in water, is insoluble in isopropanol, as are many other water-soluble polymers such as polyDADMAC, alginate, polyacrylate, and even poly(vinyl alcohol). The vast majority of both natural and synthetic polymers are not soluble in isopropanol. The further requirement that the polymer also be insoluble in water makes the selection of useful polymers for the practice of this invention even more critical.

The alcohol-containing solvent may serve a two-fold purpose, not only as a carrier, but also as an immediate disinfectant. After the alcohol-containing solvent has evaporated, a coating of the antimicrobial polymer remains on the skin or other substrate. This coating is durable, and because it is insoluble in water, it is not easily removed by, for example, perspiration, incidental contact with aqueous fluids, or light washing with aqueous fluids.

It is an aspect of the current invention that an alcohol is used as solvent and as carrier, including, but not limited to, ethanol, methanol, isopropanol, and mixtures thereof. It is an aspect of one exemplary embodiment of the invention that the alcohol solvent is denatured alcohol, specifically Denatured Alcohol SDA 3-C, which is a commercial, non-beverage grade, denatured alcohol defined by the Alcohol and Tobacco Tax Division of the Internal Revenue Service as ethanol with a 5% isopropanol denaturant (i.e., 95% ethanol/5% isopropanol).

The antimicrobial polymer may also be soluble in other organic solvents such as acetone, methyl ethyl ketone, tetrahydrofuran, ethyl acetate, ethers, esters, benzene, toluene, carbonates, hydrocarbons, or chlorinated hydrocarbons, and solutions of the antimicrobial polymer in any of these solvents may be used to prepare the antimicrobial composition; however, these solvents may not necessarily provide the advantage of immediate disinfection such as provided by alcohol.

It is a feature of this invention that the antimicrobial properties are permanently locked into the polymer structure. This can be accomplished, for example, by incorporating chemical functionalities with antimicrobial properties directly into the molecular structure of the polymer. This provides not only durability and persistence of antimicrobial effect, but also prevents soluble antimicrobial components, e.g. those of low molecular weight, from leaching from the antimicrobial coating and entering the substrate, or migrating to areas where it is not desirable to have antimicrobial activity. For instance, when applied to skin, the composition will provide persistent antimicrobial activity; however, antimicrobial activity will not migrate from the polymer and penetrate the skin surface or enter into cells where it may have undesirable effects, after evaporation of the alcohol-based carrier solvent.

It is an advantage of the current invention that the composition would be useful to protect individuals at risk of contacting biological warfare agents (e.g. military personnel and postal workers), either by treating their skin or by treating the surfaces of equipment and materials that these individuals contact.

It is an aspect of the current invention that a composition of the present invention may be used on animal skin (e.g. sanitization of cow teats, surgical procedures, and veterinary procedures).

An advantage of this invention is that it utilizes quaternary ammonium compounds as the active antimicrobial agent, and quaternary ammonium compounds do not promote the development of resistant organisms such as MRSA or VRE. Examples are provided below to demonstrate the efficacy of the materials of the current invention against such organisms.

The disinfectant composition of the present invention may additionally contain other inert or active ingredients. For example, thickening agents may be included in order to increase viscosity or to provide a gel form of the product. Additives, such as moisturizers, vitamins, UV absorbers, drugs, antimicrobials, or other inert and active agents, may also be added. Such additives do not need to be water-insoluble, as they may serve their purpose by acting transiently or otherwise may be entrapped in the polymeric coating and thereby stabilized against easy removal by aqueous fluids. In addition, permanent or temporary dyes may be added to the composition, or alternatively applied to the polymeric coating after it has been applied to the surface, in order to serve as a visual indicator of the presence of the polymeric coating.

Although the composition of the current invention provides a polymer film or coating with non-leaching antimicrobial properties, it may be desirable in some circumstances to incorporate an additional antimicrobial or antiseptic agent into the composition in order to provide additional efficacy. This additional agent is not covalently bonded to the polymer, and thus may be leachable. This does not alter the non-leachable nature of the previously-described antimicrobial polymer. When the additional antimicrobial agent has been fully leached from the composition, the antimicrobial polymer will still provide non-leachable antimicrobial activity. Furthermore, the antimicrobial polymer matrix can serve to slow the leaching rate of the additional agent, thus prolonging the efficacy of the added agent. Examples of useful antimicrobial or antiseptic additives include quaternary ammonium salts, biguanides, and phenolic compounds. In certain embodiments the added antimicrobial or antiseptic is a quaternary ammonium salt, such as benzalkonium chloride, benzethonium chloride, dimethyldidecylammonium chloride, or mixtures thereof.

In another embodiment the added antimicrobial or antiseptic is a biguanide, such as chlorhexidine or poly(hexamethylene biguanide). In another embodiment, the added antimicrobial or antiseptic is a phenolic compound, such as phenol or triclosan.

It is an aspect of the current invention that the composition may be formulated as a liquid, gel, foam, or aerosol spray and may be applied to a surface, including the skin of a human or other animal, in order to achieve a prolonged antimicrobial effect.

The examples that follow demonstrate the synthesis and application of alcohol-soluble, water-insoluble, antimicrobial polymeric molecules. It is an aspect of the invention that these polymeric molecules can be synthesized by free radical vinyl polymerization of, generally, a mixture of two different monomers, a first monomer (A) and a second monomer (B), at least one of which contains quaternary ammonium groups. The first monomer (A), and homopolymers of monomer A, are generally water-soluble, while the second monomer (B) is generally water-insoluble. A mutually effective solvent (such as alcohol) for monomers A & B may be used to prepare a homogeneous solution suitable for copolymerization of the two monomers. The copolymer of A+B, is soluble in alcohol. It should be understood that this is just one possible illustrative method to formulate the composition and one skilled in the art will realize that there are numerous other methods that can be used to prepare the alcohol-soluble, water-insoluble, antimicrobial polymeric molecules. Mixtures of three or more monomers may also be used to prepare suitable antimicrobial copolymers.

It is an aspect of this invention that the polymeric molecules can be synthesized by step-growth polymerization, such as by the reaction of a difunctional alcohol with a diisocyanate to form a polyurethane polymer. It is an aspect of this invention that other types of step-growth polymers may also be utilized including, but not limited to, polyamides (nylons), polyesters, and polyureas. The incorporation of the antimicrobial moiety into the polymer may be accomplished by utilizing an antimicrobial compound with reactive functionality. For instance, Akzo Nobel offers a range of polyoxyethylenemonoalkylmethylammonium salts sold under the tradename of Ethoquad. An example is Ethoquad C/12-75DK, which is a methyl/C12 quaternary ammonium compound with two reactive hydroxyethyl substituents that can be reacted with a diisocyanate such as tolylene-2,4-diisocyanate (TDI) to form an antimicrobial polyurethane polymer which contains quaternary ammonium moieties in the polymer main-chain structure.

In one embodiment of this invention, a dye molecule may be incorporated into, or covalently bonded to, the antimicrobial polymer structure in order to provide a nonleaching visible marker for the composition. For instance, the fluorescein dye molecule contains two hydroxyl groups which may be reacted with a diisocyanate to form part of a polyurethane structure. When a mixture of fluorescein and Ethoquad C/12-75DK is reacted with TDI, the resulting polymer contains both dye (fluorescein) and antimicrobial (quaternary ammonium) units in the polymer main-chain structure.

The antimicrobial moieties may also be incorporated into the polymer after formation of the polymer. This can be achieved, for example, by transesterification or other substitution reactions, such as the reaction of Ethoquad with a polyacrylate.

The polymer molecules synthesized will have an average degree of polymerization of 5 to 25,000 (monomeric moieties per molecule), but more preferably 50 to 10,000, and most preferably 100 to 5000. Suitable vinyl monomers for use in generating the polymer include, but are not limited to, allyl-containing monomers, vinyl-containing monomers, styrene derivatives, allyl amines, ammonium salts, acrylates, methacrylates, acrylamides, methacrylamides, dimethylaminoethyl methacrylate (methyl chloride quaternary), dimethylaminoethyl methacrylate (benzyl chloride quaternary), dimethylaminoethyl acrylate (methyl chloride quaternary), dimethylaminoethyl acrylate (benzyl chloride quaternary), and other compounds with the structure $CH_2=CR—(C=O)—X—(CH_2)_n—N^+R'R''R'''//Y^-$ (where R is hydrogen or methyl, n equals 2 or 3, X is either O, S, or NH, R', R", and R'" are independently selected from the group consisting of H, C1 to C16 alkyl, aryl, arylamine, alkaryl, and aralkyl, and Y⁻ is an anionic counterion to the positive charge of the quaternary nitrogen; diallyldimethylammonium salts; vinyl pyridine and salts thereof; and vinylbenzyltrimethylammonium salts).

Suitable free radical initiators for use in generating the polymer include, but are not limited to, azo compounds, such as AIBN and related compounds, and peroxides, such as benzoyl peroxide, dicumyl peroxide, t-butyl hydroperoxide, sodium persulfate, hydrogen peroxide, sodium peroxide, and other peroxides and hydroperoxides commonly used as free radical polymerization initiators. Photoinitiated polymerization may also be used wherein a suitable photoinitiator (e.g. a benzophenone derivative) is used which initiates polymerization upon exposure to light. Radiation polymerization may also be used, wherein polymerization is initiated by exposure to ionizing radiation (e.g. gamma rays).

Various testing methods may be employed to measure the antimicrobial efficacy of the antimicrobial polymers and compositions described herein. The "Carrier Persistence Test", or CPT, is described below. The compositions and materials of this invention have been found to give excellent results when tested by the CPT. Reductions of bacterial populations generally exceed 6 logs (99.9999% reduction of viable organisms). The materials described by this invention are capable of producing a 3-log reduction of bacteria when tested using the CPT method. Preferably, the materials described by this invention are capable of producing a 4-log reduction of bacteria when tested using the CPT method. More preferably, the materials described by this invention are capable of producing a 5-log reduction of bacteria when tested using the CPT method. Still more preferably, the materials described by this invention are capable of producing a 6-log reduction of bacteria when tested using the CPT method. It should be understood that the CPT is a comparative test in which the antimicrobial materials are compared to control materials not treated with antimicrobial agent. The maximum theoretical log reduction obtainable in a particular CPT test is limited by the growth of the bacterial population on the untreated control. Thus, it is possible to obtain virtually 100% elimination of viable organisms even though the actual log reduction is below a specified number.

EXAMPLES

The following Examples are provided to illustrate the invention and teach those skilled in the art how to make and how to use the subject matter. They are not to be read as limiting the scope of the invention.

Example A1

Co-polymerization of (2-(methacryloyloxy)ethyl)trimethylammonium chloride and butyl methacrylate A solution was made by dissolving 2.5 grams of quaternary vinyl monomer (2-(methacryloyloxy)ethyl)trimethylammonium chloride 75% aqueous solution (Aldrich Chemical Co.)), 7.5 grams of butyl methacrylate (Aldrich Chemical Co.), and 0.1 gram or AIBN (2,2'-azobis(2-methylpropionitrile) (Aldrich Chemical Co.) in 10 grams of ethanol. The solution was sparged for 60 seconds with argon gas to expel dissolved oxygen and then sealed in a glass vial under an argon atmosphere. The vial was placed in a 70° C. oven for 24 hours. The copolymer containing solution was then diluted in ethanol (1:25).

Example A2

Application of the Composition to Skin

Approximately 1 mL of the solution generated in Example A1 was placed on the skin on the back of the hand of a human volunteer, then spread and rubbed with a gloved finger until dry. After drying, an inconspicuous film remained, which was not sticky or tacky, and was virtually imperceptible to the volunteer. Bromthymol blue (BTB) indicator dye is known to bind strongly to quaternary ammonium compounds. To visualize the presence of the polymeric coating, the area of the hand to which the polymer-containing solution was applied was rinsed with a 0.5% aqueous solution of BTB indicator dye adjusted to a pH 10. The hand was rinsed under tepid running tap water for 30 seconds with light digital manipulation to remove excess BTB indicator dye solution. The area of skin treated with the copolymer solution exhibited a blue/green color, while the surrounding skin did not, indicating presence of the applied polymer. Only after vigorous scrubbing with a detergent solution, was the coating diminished to the extent that the BTB indicator dye assay no longer indicated the presence of the polymeric coating.

Example A3

Co-polymerization of (vinylbenzyl)trimethylammonium chloride and butyl methacrylate (H-1)

A solution was made by dissolving 2.5 grams of quaternary vinyl monomer (vinylbenzyl)trimethylammonium chloride (Aldrich Chemical Co.), 7.5 grams of butyl methacrylate (Aldrich Chemical Co.), and 0.1 grams of AIBN (2,2'-azobis (2-methylpropionitrile) (Aldrich Chemical Co.), in 20 grams of methanol. This solution was sparged for 60 seconds with argon gas to expel dissolved oxygen, and then sealed in a glass vial under an argon atmosphere. The vial was placed in a 70° C. oven for 24 hours. The copolymer containing solution was then diluted in ethanol (1:2). This composition was designated as "H-1" and is referred to in subsequent examples.

Example A4

Application of the Composition to Polypropylene

The solution generated in Example A3 was used to coat the interior surface of several 15 mL polypropylene centrifuge tubes by filling them with the solution and leaving them filled overnight. The solution was then poured off and the alcohol was evaporated completely in a low temperature oven set to 50° C. To visualize the presence of polymeric coating on the inside of the tubes, approximately 5 mL of 0.5% aqueous solution of BTB indicator dye was added to one of the tubes and then shaken to coat the entire inside of the tube. After rinsing the tube several times with distilled water, the interior surface of the tube remained a deep blue color, indicating that the inner surface of the tube was coated with water-insoluble polymer.

Example A5

Antimicrobial Activity of Polymeric Composition

A 2 mL aliquot of a $10^{-4}$ dilution of an overnight culture of *S. aureus* (~$1\times10^8$ CFU/mL) was added to one polypropylene centrifuge tube treated as in Example A4 (sample) and to one untreated polypropylene centrifuge tube (control). During overnight incubation at 37° C., the tubes were slowly rolled to ensure contact between the bacteria culture and the interior surface of the tubes. The next day, serial dilutions of the bacteria cultures harvested from each tube were streaked onto bacteria culture plates. The culture harvested from the untreated control tube yielded $2.5\times10^4$ CFU, while zero colonies were observed on plates streaked with cultures harvested from the treated sample tubes. The difference in the number of colonies enumerated translates into at least a 4.4 log reduction in the bacterial population.

Example A6

Synthesis of a Quaternary Ammonium Polyurethane (H3-C) that is Soluble in Alcohol, but Insoluble in Water Fifty grams of Ethoquad C/12-75DK (Akzo Nobel) was placed in a round-bottom flask on a rotary evaporator and evaporated to dryness. The residue (~37.5 grams) was redissolved in 70 mL tetrahydrofuran (THF) with agitation at approximately 50° C. Forty grams of tolylene-2,4-diisocyanate (TDI) was added and the solution was mixed for one hour while immersed in a water bath held at ~50° C. The viscosity of the solution increased during this time, and the solution remained clear when cooled to room temperature. The solution was stored overnight at room temperature and some additional increase in viscosity was observed. Nine grams of dipropylene glycol was added, and the solution was mixed for four hours at 50° C. The mixture was then placed on a rotary evaporator to remove all volatile solvent (primarily THF) by vacuum stripping at ~50° C. The mixture was then dissolved in 100 mL of isopropanol, and the vacuum stripping was repeated. The mixture was then dissolved in 100 mL of isopropanol once again, and the vacuum stripping was again repeated. The mixture was then redissolved in 100 mL of isopropanol to give a clear, viscous, yellowish solution with a solid polymer content of ~56 wt %. The polymer solution was subsequently diluted to various concentrations ranging from 1% to 10% solids, and these solutions were used to coat various objects such as glass slides and polypropylene test-tubes. The coatings were clear to slightly opaque when dry, were non-tacky, and were adherent to the substrate. Furthermore, the coatings were not removed by rinsing in water or saline solution. The product polymer is believed to comprise a linear polyurethane with quaternary ammonium units in the main-chain structure of the polymer. The product of this example was coded as "H3-C", and is used as an antimicrobial coating in some of the following examples.

Example A7

Synthesis of a Quaternary Ammonium Polyurethane (H3-F) Containing Covalently-Bonded Fluorescein Moieties, which is Soluble in Alcohol, but Insoluble in Water Fifty milligrams of fluorescein dye (neutral molecule) was dissolved in 3 mL of THF, and then mixed with eight grams of tolylene-2,4-diisocyanate (TDI). This solution was mixed for one hour at ~50° C., and then stored overnight at room temperature before being mixed with ten grams of Ethoquad C/12-75DK (Akzo Nobel), which had previously been vacuum stripped to remove the isopropanol solvent and redissolved in 14 grams tetrahydrofuran (THF) with agitation at approximately 50° C. This mixture was then mixed for several hours at ~50° C., and then subjected to vacuum stripping. The mixture was redissolved in isopropanol and then vacuum stripped. The dissolution/stripping was repeated one additional time, and the product was dissolved in ~50 mL isopropanol. The solution was found to have a solids content of 17.4 wt %. The product of this reaction is expected to be fluorescein-labeled linear polyurethane containing quaternary ammonium moieties in the polymer main-chain structure. Additionally, the polymer is expected to contain fluorescein moieties in the polymer main-chain structure. The fluorescein moieties provide a useful diagnostic tool to measure the presence, dispersion, persistence, and migration of the polymer. Coatings were prepared on various substrates as described in the preceding example, and the coatings had similar properties to those described above. Coated glass microscope slides were placed into 50 mL culture tubes containing either 15 mL of deionized water or 15 mL of phosphate buffered saline and place in a shaking incubator for several hours at 37° C. The solutions were then analyzed by visible spectroscopy (Spectronic 20) at 495 nm. No leaching of fluorescein could be detected, indicating complete incorporation of the dye into the polymer structure.

Example A8

Preparation of an Antimicrobial Coating Composition

Appropriate amounts of the quaternary polyurethane described above (H3-C) and glycerol were diluted in isopropanol to give a composition that contained 10 wt % H3-C and 5 wt % glycerol. The solution remained clear, and the film forming and adherent properties of the polymer were not adversely affected when coatings were prepared on glass slides.

Example A9

Preparation of an Antimicrobial Coating Composition Containing a Skin Emollient (SS-1C)

Appropriate amounts of the quaternary polyurethane described above (H3-C) and glycerol were diluted in isopropanol in order to give a final composition that contained 10 wt % H3-C, 5 wt % propylene glycol, and 5% dipropylene glycol, with the balance being isopropanol (80 wt %). The solution remained clear, and the film forming and adherent properties, as well as the antimicrobial efficacy of the polymer were not adversely affected when coatings were prepared on glass slides or pig skin. Propylene glycol and dipropylene glycol are known to have emollient properties and are widely used in topical skin products such as lotions and cosmetics.

Example A10

Preparation of an Antimicrobial Coating Composition Containing a Skin Emollient The formulation of Example A9 (SS-1C) was diluted with isopropanol at ratios of one part SS-1C to one part isopropanol, and one part SS-1C to three parts isopropanol.

Example A11

Preparation of an Antimicrobial Coating Composition Containing a Skin Emollient and UV Absorber The formulation of EXAMPLE A9 (SS-1C) is modified to include UV-absorbing or UV-blocking sunscreen ingredient in order to protect the skin from absorption of UV rays and to prevent sunburn. The UV-absorbing or UV-blocking additive is selected from the list comprising: para-aminobenzoic acid (PABA), PABA esters, cinnamates, benzophenes, salicylates, octocrylene, dibenzoyl-methane, avobenzone, oxybenzone, zinc oxide, and titanium dioxide.

Example A12

Preparation of an Antimicrobial Coating Composition Containing a Skin Emollient and Vitamin E The formulation of Example A9 (SS-1C) is modified to include 1% vitamin E. Vitamin E is practically insoluble in water, but freely soluble in alcohol.

Example A13

Preparation of an Antimicrobial Coating Composition Containing an Antimicrobial Additive (SS1C-BAC3)

An antimicrobial coating composition (SS1C-BAC3) is prepared by mixing 1.1 grams of benzalkonium chloride with 35.5 grams of the formulation of Example A9 (SS-1C). The benzalkonium chloride fully dissolved and the solution was clear and colorless. This composition was tested for antimicrobial efficacy using a modified version of ASTM test method #E 1874-97 ("*Standard Test Method for Evaluation of Antibacterial Washes by Cup Scrub Technique*"), as described below. Variations included using harvested pig skin from a slaughterhouse rather than live human volunteers. In addition to the SS1C-BAC3 material, a placebo was formulated which consisted of 5% propylene glycol and 5% dipropylene glycol in isopropanol. Results are presented below.

Summary and Results of Modified Cup Scrub Technique for Pig Skin

1. Preparation and Sterilization of Pig Skin Samples 1.1 Nine total samples were used in this method—3 samples for test product (SS1C-BAC3), 3 for placebo, and 3 for negative controls. The samples were cut out of a sheet of pig skin by tracing the bottom of a Petri dish onto the skin and cutting out the circular piece, so that the samples were an appropriate size to completely line the bottom of the Petri dish. Each of the 9 samples were cut from the sheet of skin and placed into the bottom of its own Petri dish, stratum corneum side up.

1.2 Once in the Petri dishes, the sample skins were wiped with a towel that was thoroughly saturated with 70% alcohol, and then placed under UV light in the BSC (biological safety cabinet) to dry for approx 10 minutes. The lids of the Petri dishes were also placed (facing up) along side of the samples under the UV light.

2. Application of Test Product and Placebo 2.1 After drying under UV light, the BSC was switched to fluorescence with the blower on, and a 1×1 in square was drawn on to each of the skins with an ink marker. This is used as the site of application. The UV light was turned on again, with the lids still facing up, for a few minutes to insure that no contamination occurred while marking the skins.

2.2 The BSC was switched back to fluorescence with the blower on, and the lids were placed back onto the Petri dishes containing the samples.

2.3 One sample at a time, the lid was lifted from the Petri dish and 0.5 mL each of the test product was applied to the first three samples (within the designated square). The sterile pipette tip was changed in between each application.

2.4 Step 2.2 is repeated 3 times with the placebo, and the remaining 3 sample skins are left as negative controls.

3. Performance of Cup Scrub Technique 3.1 Once the product and placebo was applied each of the 9 samples were left covered in the BSC, and one sample was brought out at a time for testing.

3.2 The cup (about 1.5 cm diameter and 1.5 in tall) was centered onto the application site of the sample with firm pressure to form a cup/skin seal. The cup was first sterilized in 95% alcohol and then flame dried. While one person maintained constant pressure on the cup to protect the cup/skin seal, another person dispensed 0.25 mL of inoculum into the cup. Once dispensed, the inoculum was left for a 5 minute exposure.

3.3 After 5 minutes, a glass rod that had been sterilized in 95% alcohol and flame dried was used to scrub around the skin within the cup for 30 seconds. After the 30 seconds the fluid was recovered with a sterile pipette into 0.5 mL of neutralizer.

3.4 Once the sample fluid was recovered, 0.25 mL of neutralizer was dispensed onto the same test site for a second recovery, and another 30 sec scrub was performed with a newly fired glass rod. The fluid was recovered into the same solution from the first scrub.

3.5 Steps 3.2-3.4 are repeated for the remaining 8 samples.

4. Data Collection

Results were quantified by making standard serial dilutions of the recovered scrub fluids and then plated using the spread plate technique. Plates were incubated over night and log reductions were calculated for both the negative control and the placebo 5. Results In tests of the product vs *E. coli*, two consecutive performances showed full kill, which corresponded to an average 4.5 log reduction in this instance.

The placebo showed no effect on the test organism.

Thin Film Efficacy Test (TFET):

Summary: The Thin Film Efficacy Test (TFET) was developed, based on [Bhende, S; Rothenburger, S; Spangler, D. J; In Vitro Assessment of Microbial Barrier Properties of Dermabond Topical Skin Adhesive. *Surgical Infections* 3 (3), pp 251-257 (2002)] to determine the bacteriostatic ability of an antibacterial solution. The procedural steps of the TFET consist of applying an antibacterial solution to appropriate growth media plates and allowing the solution to completely dry. The plates are then inoculated with ~1×10$^{-6}$ CFU/ml of desired organism and subsequently incubated overnight after inoculum has completely absorbed. The area of application is then checked for bacteriostatic activity.

| | |
|---|---|
| Plates: | The media plates used for this assay are selective media plates that are appropriate to the respective organisms. Sixty plates are used for each organism. |
| | MSA: MSA (Mannitol Salt Agar) is the selective media for *S. aureus* and MRSA. |
| | EMB: Eosin Methylene Blue Agar is the selective media for *E. coli*. |
| | EA: *Enterococcosel* Agar is the selective media for VRE. |

-continued

| | |
|---|---|
| Coating: | 100 μl of the antibacterial solution is applied to each plate and allowed to air dry for a minimum of 1 hour in the biological safety cabinet before inoculating. |
| Inoculating: | The test organism is grown in the appropriate growth media and incubated overnight unless otherwise specified. The inoculum is made to achieve a titer of $10^6$ CFU/ml. The coated plates are then inoculated with 1000 μl bacterial solution and the inoculum is then homogenously applied by moving the plate in a circular motion. |
| Exposure: | The samples are incubated at 37° C. in a high humidity chamber and the exposure time is overnight unless otherwise stated. |
| Results: | After incubation, each plate is inspected for bacteriostatic activity on the area of application. The results are read as Pass/Fail. If there is no growth, the plate is read as Pass and if there is growth on the area, the plate is read as Fail. |

TFET—Results:

Example T1

The Thin Film Efficacy Test (TFET) was used to determine the bacteriostatic ability of the antimicrobial solution. The procedural steps of the TFET consist of using growth media plates as carriers in which 100 μl of the chosen antimicrobial solution is applied in the center of the plate. The antimicrobial solution was allowed to air dry for a minimum of 1 hour prior to inoculation. The coated plates were inoculated with 1000 μl inoculum at a titer of $10^6$ CFU/ml. The inoculum was homogeneously applied by swirling the plate until the inoculum completely covered the entire surface area of the plate. The inoculated plates were then allowed to dry and subsequently incubated overnight at 37° C. Following overnight incubation, the area of antimicrobial solution application was checked for suppression of bacterial growth and the results were read as Pass/Fail. If suppression of growth was observed, the plate was considered passing. If no suppression of growth as observed, the plate was considered failing. The media used for *S. aureus*, ATCC #6538, was Mannitol Salt Agar (MSA) and the antimicrobial solution used was H3-C (From Example A6).

The results for *S. aureus* were as follows:

| Antimicrobial Solution | 24 hr Results | 48 hr Results |
|---|---|---|
| 5% H3-C | 60 Pass/0 Fail | 60 Pass/0 Fail |
| 10% H3-C | 60 Pass/0 Fail | 60 Pass/0 Fail |

Example T2

Example T2 uses Methicillin-Resistant *S. aureus* (MRSA, ATCC #BAA-44) as the test organism and again MSA is used as the growth media.

The results for MRSA are as follows:

| Antimicrobial Solution | 24 hr Results | 48 hr Results |
|---|---|---|
| 5% H3-C | 60 Pass/0 Fail | 60 Pass/0 Fail |

Example T3

Example T3 used *E. coli*, ATCC #15597, as the test organism and additionally Eosin Methylene Blue Agar was used as the growth media.

The results for *E. coli* were as follows:

| Antimicrobial Solution | 24 hr Results | 48 hr Results |
|---|---|---|
| 5% H3-C | 60 Pass/0 Fail | 60 Pass/0 Fail |
| 10% H3-C | 60 Pass/0 Fail | 60 Pass/0 Fail |

Example T4

Example T4 used Vancomycin-Resistant *Enterococcus* (VRE, ATCC # 700221) as the test organism and additionally used Enterococcosel Agar as the growth media.

The results for VRE were as follows:

| Antimicrobial Solution | 24 hr Results | 48 hr Results |
|---|---|---|
| 5% H3-C | 60 Pass/0 Fail | 60 Pass/0 Fail |

Example T5

Example T5 used the H-1 formulation (see Example A3) as the antimicrobial solution. The results for *S. aureus* were as follows:

| Antimicrobial Solution | 24 hr Results | 48 hr Results |
|---|---|---|
| 10% H-1 | 60 Pass/0 Fail | 60 Pass/0 Fail |

Example T6

Example T6 also used the H-1 formulation as the antimicrobial solution.

The results for *E. coli* were as follows:

| Antimicrobial Solution | 24 hr Results | 48 hr Results |
|---|---|---|
| 10% H-1 | 60 Pass/0 Fail | 60 Pass/0 Fail |

Comparative Example T7

For comparison with compositions of the present invention, Example T7 used Zero brand hand sanitizer (Aquagen International, Inc.) as the antimicrobial solution.

The results for *S. aureus* were as follows:

| Antimicrobial Solution | 24 hr Results | 48 hr Results |
|---|---|---|
| Zero | 8 Pass/52 Fail | 0 Pass/60 Fail |

Comparative Example T8

For comparison with compositions of the present invention, Example T8 also used Zero brand hand sanitizer as the antimicrobial solution.

The results for *E. coli* were as follows:

| Antimicrobial Solution | 24 hr Results | 48 hr Results |
|---|---|---|
| Zero | 0 Pass/60 Fail | 0 Pass/60 Fail |

Comparative Example T9

For comparison with compositions of the present invention, Example T9 used Purell brand hand sanitizer (GOJO Industries, Inc.) as the antimicrobial solution.

The results for *S. aureus* were as follows:

| Antimicrobial Solution | 24 hr Results | 48 hr Results |
|---|---|---|
| Purell | 0 Pass/60 Fail | 0 Pass/60 Fail |

Comparative Example T10

For comparison with compositions of the present invention, Example T10 also used Purell brand hand sanitizer (GOJO Industries, Inc.) as the antimicrobial solution.

The results for *E. coli* were as follows:

| Antimicrobial Solution | 24 hr Results | 48 hr Results |
|---|---|---|
| Purell | 0 Pass/60 Fail | 0 Pass/60 Fail |

Carrier Persistence Test (CPT):

Summary: This procedure is a modification of the EPA's Standard Operating Procedure:
Testing of Spray Disinfectants against *Staphylococcus aureus, Pseudomonas aeruginosa*, and *Mycobacterium bovis;*
which is an adaptation of the AOAC method to determine the efficacy of spray products as hard surface disinfectants against three test organisms, *Mycobacterium bovis* (BCG), *Pseudomonas aeruginosa*, and *Staphylococcus aureus*.

The procedural steps of the CPT consist of applying an antimicrobial test solution to chosen carriers and allowing the carriers to dry before they are inoculated with the appropriate test organism. After inoculation, the carriers are incubated for the prescribed exposure time, subsequently placed into neutralizing solution, then serial diluted and plated for efficacy quantification using standard methods.

| | |
|---|---|
| Carriers: | The carriers are 25 cm$^2$ and can be comprised of a variety of materials. The carriers are sterilized by methods appropriate to the carrier's composition. The three carriers types used in these assays are borosilicate glass, Vitro-Skin, and pig skin; however, carriers suitable for use in this method are not limited to the aforementioned. |
| Borosilicate Glass: | Borosilicate glass slides are washed with ethanol and allowed to air dry. After drying, the borosilicate glass slides are placed into Petri dishes and autoclaved for 15 minutes. |
| Vitro-Skin: | The Vitro-Skin is prepared according to manufacturer's specifications. If Vitro-Skin becomes unsterile, it needs to be sterilized with 70% alcohol, allowed to dry, and re-hydrated according to the manufacturer's specifications. Vitro-Skin was directly purchased from the manufacturer (IMS Inc., Orange, CT). VITRO-SKIN is an advanced testing substrate that effectively mimics the surface properties of human skin. It contains both optimized protein and lipid components and is designed to have topography, pH, critical surface tension and ionic strength similar to human skin. |
| Pig Skin: | The pig skin is sterilized with 70% alcohol. This procedure includes thoroughly wetting the carriers with the 70% alcohol and allowing the carriers to thoroughly air dry in a Biological Safety Cabinet (BSC). As an alternative, the pig skin may be exposed to UV light for 10 minutes. Fresh pig skin is purchased from a local slaughterhouse. |
| Application: | The antimicrobial solution is applied to each carrier until it thoroughly wets the carriers. The solution volume should not exceed 1000 µl and will not be less than 20 µl. The antimicrobial solution is then allowed to air dry for a minimum of 1 hour in a BSC before inoculating. |
| Inoculation: | Test organisms are grown in appropriate growth media and incubated overnight at 37° C. unless otherwise specified. The inoculum is modified to produce a titer of 10$^8$ CFU/ml. The carriers carrying the antimicrobial solution is then inoculated with 10 µl-20 µl of inoculum. The inoculum will be distributed with sterile swabs saturated with inoculum. Exposure time begins directly after inoculation. |
| Exposure: | The exposure time is overnight unless otherwise specified and samples are incubated at 37° C. in a high humidity chamber. |
| Neutralization: | Inoculated carriers are neutralized before recovering the organisms to stop antimicrobial activity of the antimicrobial solution. All neutralizations are done with 20 ml aliquots of Letheen Broth in 50 ml conical centrifuge tubes at a minimum of 10 minutes unless otherwise specified. |
| Recovery: | Organism recovery is started within the neutralization tubes. The neutralized carriers are vortexed for 1 minute and the organisms are subsequently recovered with standard serial dilution and plating methods. Plates are incubated overnight at 37° C. and colony forming units are quantified the following day. |
| Controls: | Carrier substrates without any applied antimicrobial coating are used as negative controls to determine the baseline microbial growth. Control substrates were of the same composition as the test substrates within each sample set. Colony counts for the control substrates are reported. |
| Calculations: | Calculations will be computed using a Microsoft Excel spreadsheet. Electronic copies of the spreadsheet as well as hard copies will be retained. |

To calculate CFU/mL per carrier:

$$[(\text{avg. CFU for } 10^{-w}) + (\text{avg. CFU for } 10^{-x}) + (\text{avg. CFU for } 10^{-y}) + (\text{avg. CFU for } 10^{-z})]/(10^{-w} + 10^{-x} + 10^{-y} + 10^{-z})$$

where $10^{-w}$, $10^{-x}$, $10^{-y}$, and $10^{-z}$ are the dilutions plated. In the event that one or more dilutions yield plate counts greater than 300, or less than 30, those counts and their corresponding dilutions will not be used in the calculations. In the event that only one of two plates has counts yielding 300 CFU or less, that plate count and its corresponding dilution will be included but no average will be determined.

NOTE: Plate counts of 0 are to be included in all calculations.

To calculate Log Reduction:

$$LR = \text{Log}[(\text{CFU/ml for treated carrier})/(\text{CFU/ml for control carrier})]$$

Carrier Persistence Test—Results:

Example C1

A 10% solution of H-1 antimicrobial polymer (See Example A3) was applied to borosilicate glass slide carriers.

Using the tip of a pipette, 250 μl of Nimbuderm H-1 was homogenously applied over the 25 cm² surface of the glass slide carrier. The glass slide carriers were allowed to dry for at least 1 hour prior to inoculation. The carriers were inoculated with 10 μl of $10^8$ CFU/ml inoculum of to ensure a target load of $10^6$ CFU/ml. The organism used was *S. aureus* ATCC #6538, and the allowed exposure time was 30 minutes. Following the exposure, the inoculated glass slide carriers were placed in neutralizing solution of 20 ml Letheen Broth for no less than 10 minutes to allow for proper neutralization—the Letheen broth was chilled to 4° C. prior to use. Following neutralization, the carriers were vortexed in the neutralization broth for one minute to facilitate the recovery of the organism. The recovery of viable organisms was done by standard serial dilution and plating methods.

Results were as Follows:
*S. aureus* control carrier population: $3.20 \times 10^6$ CFU/ml
Carrier: Borosilicate glass slides
Exposure time: 30 min

| Samples | Solution | Log Reduction |
|---|---|---|
| 1 | 10% H-1 | 6.51* |
| 2 | 10% H-1 | 6.51* |
| 3 | 10% H-1 | 6.51* |
| 4 | 10% H-1 | 6.51* |

(*= full kill)

Example C2

Example C2 is identical to Example C1 with the exception to the exposure time. The exposure time used for Example C2 was 16 hours (overnight exposure).

Results were as Follows:
*S. aureus* control carrier population: 2.30E07 CFU/ml
Carrier: Borosilicate glass slides
Exposure time: 16 hours

| Samples | Solution | Log Reduction |
|---|---|---|
| 1 | 10% H-1 | 7.36* |
| 2 | 10% H-1 | 7.36* |
| 3 | 10% H-1 | 7.36* |
| 4 | 10% H-1 | 7.36* |
| 5 | 10% H-1 | 7.36* |
| 6 | 10% H-1 | 7.36* |

(*= full kill)

Example C3

Example C3 is identical to Example C2 with the exception of the organism. The organism used was *E. coli* ATCC 15597.

Results were as Follows:
*E. coli* control carrier population: 1.06E05 CFU/ml
Carrier: Borosilicate glass slides
Exposure time: 16 hours

| Samples | Solution | Log Reduction |
|---|---|---|
| 1 | 10% H-1 | 5.03* |
| 2 | 10% H-1 | 5.03* |
| 3 | 10% H-1 | 5.03* |
| 4 | 10% H-1 | 5.03* |
| 5 | 10% H-1 | 5.03* |
| 6 | 10% H-1 | 5.03* |

(*= full kill)

Example C4

Example C4 is identical to Example C3 with the exception of the carrier. The carrier used was Vitro-Skin.

Results were as Follows:
*E. coli* control carrier population: 2.87E06 CFU/ml
Carrier: Vitro-Skin
Exposure time: 16 hours

| Samples | Solution | Log Reduction |
|---|---|---|
| 1 | 10% H-1 | 6.46* |
| 2 | 10% H-1 | 6.46* |
| 3 | 10% H-1 | 6.46* |
| 4 | 10% H-1 | 6.46* |
| 5 | 10% H-1 | 6.46* |
| 6 | 10% H-1 | 6.46* |

(*= full kill)

Example C5

A 10% solution of H-3 antimicrobial polymer (see Example A6) was applied to borosilicate glass slide carriers. Using the tip of a pipette, 250 μl of H-3 (10% polymer content) was homogenously applied over the 25 cm² surface of the glass slide carrier. The glass slide carriers were allowed to dry for at least 1 hour prior to inoculation. The carriers were inoculated with 10 μl of $10^8$ CFU/ml inoculum to ensure a target load of $10^6$ CFU/ml. The organism used was *S. aureus* ATCC #6538 the allowed exposure time was 30 minutes. Following the exposure, the inoculated glass slide carriers were placed in neutralizing solution of 20 ml Letheen Broth for no less than 10 minutes to allow for proper neutralization. The Letheen broth was chilled to 4° C. prior to use. Following neutralization, the carriers were vortexed in the neutralization broth for one minute to facilitate the recovery of the organism. The recovery of viable organisms was performed by standard serial dilution and plating methods.

Results were as Follows:
*E. coli* control carrier population: 1.06E05 CFU/ml
Carrier: Borosilicate glass slides
Exposure time: 16 hours

| Samples | Solution | Log Reduction |
|---|---|---|
| 1 | 10% H-3 | 5.03* |
| 2 | 10% H-3 | 5.03* |
| 3 | 10% H-3 | 5.03* |
| 4 | 10% H-3 | 5.03* |
| 5 | 10% H-3 | 5.03* |
| 6 | 10% H-3 | 5.03* |

(*= full kill)

Example C6

Example C6 is identical to Example C5 with the exception of the carrier. The carrier used was Vitro-Skin.
Results were as Follows:
E. coli control carrier population: 2.87E06 CFU/ml
Carrier: Vitro-Skin
Exposure time: 16 hours

| Samples | Solution | Log Reduction |
| --- | --- | --- |
| 1 | 10% H-3 | 6.46* |
| 2 | 10% H-3 | 6.46* |
| 3 | 10% H-3 | 6.46* |
| 4 | 10% H-3 | 6.46* |
| 5 | 10% H-3 | 6.46* |
| 6 | 10% H-3 | 6.46* |

(*= full kill)

Example C7

Example C7 is identical to Example C5 with the exception of the concentration of skin sanitizer solution. The H3-C skin sanitizer's concentration is now reduced to 7%.
Results were as Follows:
E. coli control carrier population: 2.50E06 CFU/ml
Carrier: Borosilicate glass slides
Exposure time: 16 hours

| Samples | Solution | Log Reduction |
| --- | --- | --- |
| 1 | 7% H3-C | 6.40* |
| 2 | 7% H3-C | 6.40* |
| 3 | 7% H3-C | 6.40* |
| 4 | 7% H3-C | 6.40* |
| 5 | 7% H3-C | 6.40* |
| 6 | 7% H3-C | 6.40* |

(*= full kill)

Example C8

Example C8 is identical to Example C7 with the exception of the carrier. The carrier used was Vitro-Skin.
Results were as Follows:
E. coli control carrier population: 2.08E06 CFU/ml
Carrier: Vitro-Skin
Exposure time: 16 hours

| Samples | Solution | Log Reduction |
| --- | --- | --- |
| 1 | 7% H3-C | 6.32* |
| 2 | 7% H3-C | 6.32* |
| 3 | 7% H3-C | 6.32* |
| 4 | 7% H3-C | 6.32* |
| 5 | 7% H3-C | 6.32* |
| 6 | 7% H3-C | 6.32* |

(*= full kill)

Example C9

Example C9 is identical to Example C7 with the exception of the concentration of skin sanitizer solution. The H3-C skin sanitizer's concentration is now further reduced to 1%.
Results were as Follows:
E. coli control carrier population: 2.77E04 CFU/ml
Carrier: Borosilicate glass slides
Exposure time: 16 hours

| Samples | Solution | Log Reduction |
| --- | --- | --- |
| 1 | 1% H3-C | 4.44* |
| 2 | 1% H3-C | 4.44* |
| 3 | 1% H3-C | 4.44* |
| 4 | 1% H3-C | 4.44* |
| 5 | 1% H3-C | 4.44* |
| 6 | 1% H3-C | 4.44* |

(*= full kill)

Example C10

Example C10 is identical to Example C9 with the exception of the organism. The organism used was S. aureus ATCC #6538.
Results were as Follows:
S. aureus control carrier population: 1.25E03 CFU/ml
Carrier: Borosilicate glass slides
Exposure time: 16 hours

| Samples | Solution | Log Reduction |
| --- | --- | --- |
| 1 | 1% H3-C | 3.10* |
| 2 | 1% H3-C | 3.10* |
| 3 | 1% H3-C | 3.10* |
| 4 | 1% H3-C | 3.10* |
| 5 | 1% H3-C | 3.10* |
| 6 | 1% H3-C | 3.10* |

Example C11

Example C11 is identical to Example C10 with the exception of the organism. The organism used was P. aeruginosa ATCC #15442.
Results were as Follows:
P. aeruginosa control carrier population: 3.93E06 CFU/ml
Carrier: Borosilicate glass slides
Exposure time: 16 hours

| Samples | Solution | Log Reduction |
| --- | --- | --- |
| 1 | 1% H3-C | 6.59* |
| 2 | 1% H3-C | 6.59* |
| 3 | 1% H3-C | 6.59* |
| 4 | 1% H3-C | 6.59* |
| 5 | 1% H3-C | 6.59* |
| 6 | 1% H3-C | 6.59* |

(*= full kill)

Example C12

A 1% solution H3-C antimicrobial polymer was applied to borosilicate glass slide carriers. The sanitizer solution was applied by passing over the 25 cm$^2$ slide surface two times using a nonwoven wipe material (polyester/cotton) saturated with sanitizer solution. The now coated glass slide carriers were allowed to dry for at least 1 hour prior to inoculation.

The coated glass slides were then inoculated with an inoculum of $10^8$ CFU/ml to ensure a target load of $10^6$ CFU/ml. The organism used was *E. coli* ATCC 15597 and the allowed exposure time was 16 hours. Following the exposure, the inoculated glass slide carriers were placed into a neutralizing solution of 20 ml Letheen Broth for no less than 10 minutes to allow for proper neutralization. The Letheen broth was chilled to 4° C. prior to use. Following neutralization, the carriers were vortexed in the neutralization broth for one minute to facilitate the recovery of the organism. The recovery of viable organisms was performed by standard serial dilution and plating methods.

Results were as Follows:
*E. coli* control carrier population: 1.57E06 CFU/ml
Carrier: Borosilicate glass slides
Exposure time: 16 hours

| Samples | Solution | Log Reduction |
|---|---|---|
| 1 | 1% H3-C | 6.19* |
| 2 | 1% H3-C | 6.19* |
| 3 | 1% H3-C | 6.19* |
| 4 | 1% H3-C | 6.19* |
| 5 | 1% H3-C | 6.19* |
| 6 | 1% H3-C | 6.19* |

(*= full kill)

Example C13

Example C13 is identical to Example C12 with the exception of the organism. The organism used was *P. aeruginosa* ATCC #15442.

Results were as Follows:
*P. aeruginosa* control carrier population: 4.70E06 CFU/ml
Carrier: Borosilicate glass slides
Exposure time: 16 hours

| Samples | Solution | Log Reduction |
|---|---|---|
| 1 | 1% H3-C | 6.67* |
| 2 | 1% H3-C | 6.67* |
| 3 | 1% H3-C | 6.67* |
| 4 | 1% H3-C | 6.67* |
| 5 | 1% H3-C | 6.67* |
| 6 | 1% H3-C | 6.67* |

(*= full kill)

Comparative Example C14

Purell brand instant hand sanitizer solution (GOJO Industries, Inc.) was applied to borosilicate glass slide carriers. Using the tip of a pipette, 250 ul of Purell was homogenously applied over the 25 cm² surface of the glass slide carrier. The glass slide carriers were allowed to dry for at least 1 hour prior to inoculation. The carriers were inoculated with 10 ul of $10^8$ CFU/ml inoculum to ensure a target load of $10^6$ CFU/ml. The organism used was *S. aureus* ATCC #6538, and the allowed exposure time was 30 minutes. Following the exposure, the inoculated glass slide carriers were placed in neutralizing solution of 20 ml Letheen Broth for no less than 10 minutes to allow for proper neutralization. The Letheen broth was chilled to 4° C. prior to use. Following neutralization, the carriers were vortexed in the neutralization broth for one minute to facilitate the recovery of the organism. The recovery of viable organisms was performed by standard serial dilution and plating methods.

*S. aureus* control carrier population: 1.02E05 CFU/ml
Carrier: Borosilicate glass slides
Exposure time: 30 minutes

| Samples | Solution | Log Reduction |
|---|---|---|
| 1 | Purell | 1.07 |
| 2 | Purell | 1.22 |
| 3 | Purell | 1.17 |
| 4 | Purell | 1.07 |
| 5 | Purell | 1.19 |
| 6 | Purell | 1.14 |

Comparative Example C15

Example C15 is identical to Example C14 with the exception of the organism. The organism used was *E. coli* ATCC #15597.

Results were as Follows:
*E. coli* control carrier population: 4.70E06 CFU/ml
Carrier: Borosilicate glass slides
Exposure time: 30 min

| Samples | Solution | Log Reduction |
|---|---|---|
| 1 | Purell | 0.89 |
| 2 | Purell | 0.50 |
| 3 | Purell | −1.46 |
| 4 | Purell | −4.95 |
| 5 | Purell | 0.75 |

Comparative Example C16

Example C16 is identical to Example C14 with the exception of the organism. The organism used was *P. aeruginosa* ATCC #15442.

Results were as Follows:
*P. aeruginosa* control carrier population: 4.70E06 CFU/ml
Carrier: Borosilicate glass slides
Exposure time: 30 min

| Samples | Solution | Log Reduction |
|---|---|---|
| 1 | Purell | 0.37 |
| 2 | Purell | 0.33 |
| 3 | Purell | 0.37 |

Example C17

The material of Example A9 (SS-1C) was applied to pig skin carriers. Using the tip of a pipette, 1000 μl of SS-1C was homogenously applied over the 25 cm² surface of the pig skin carrier. The pig skin carriers were allowed to dry for at least 1 hour prior to inoculation. The carriers were inoculated with 20 μl of $10^8$ CFU/ml inoculum of to ensure a target load of $10^6$ CFU/ml. The organism used was *Serratia. marcescens*, ATCC #13380. The allowed exposure time was 4 hours. Following the exposure, the inoculated pig skin carriers were placed in neutralizing solution of 20 ml Letheen Broth for no less than 10 minutes to allow for proper neutralization—the Letheen broth was chilled to 4° C. prior to use. Following neutralization, the carriers were vortexed in the neutralization broth for one minute to facilitate the recovery of the organism. The recovery of viable organisms was done by standard serial dilution and plating methods.

Results were as Follows:
S. marcescens control carrier population: 1.18E07 CFU/ml
Carrier: Pig Skin
Exposure time: 4 hours

| Samples | Solution | Log Reduction |
|---|---|---|
| 1 | 10% SS-C | 7.07 |
| 2 | 10% SS-C | 7.07 |
| 3 | 10% SS-C | 7.07 |

Example C18

Example C18 is identical to Example C17 with the exception of the organism. The organism used was E. coli ATCC 8739.

Results were as Follows:
E. coli control carrier population: 1.54E07 CFU/ml
Carrier: Pig Skin
Exposure time: 4 hours

| Samples | Samples | Log Reduction |
|---|---|---|
| 1 | 10% SS-C | 7.19 |
| 2 | 10% SS-C | 7.19 |
| 3 | 10% SS-C | 7.19 |

Example C19

Example C19 is identical to Example C17 with the exception of the organism. The organism used was MRSA (Methacillin-resistant Staph. aureus)

Results were as Follows:
MRSA control carrier population: 2.63E07 CFU/ml
Carrier: Pig Skin
Exposure time: 4 hours

| Samples | Solution | Log Reduction |
|---|---|---|
| 1 | 10% SS-C | 7.42 |
| 2 | 10% SS-C | 7.42 |
| 3 | 10% SS-C | 7.42 |

Example C20

Example C20 is identical to Example C17 with the exception of the organism. The organism used was VRE, (Vancomycin resistant Enterococcus)

Results were as Follows:
VRE control carrier population: 3.23E06 CFU/ml
Carrier: Pig Skin
Exposure time: 4 hours

| Samples | Solution | Log Reduction |
|---|---|---|
| 1 | 10% SS-C | 6.51 |
| 2 | 10% SS-C | 6.51 |
| 3 | 10% SS-C | 6.51 |

Having thus described the invention, what is desired to claim and thereby protect by Letters Patent is:

1. An antimicrobial composition comprising a polyurethane polymer dissolved in a solvent consisting essentially of alcohol, the polyurethane polymer being readily soluble in the solvent but insoluble in water,
    wherein the polyurethane polymer comprises monomeric moieties containing at least one quaternary ammonium group,
    wherein said monomeric moieties provide at least 10% of the total weight of said polyurethane polymer and are incorporated into the molecular structure of the polyurethane polymer by covalent chemical bonding via either polymerization with other monomers or reaction with an existing polymer, and
    wherein said quaternary ammonium group is in the main-chain of the polyurethane polymer,
    whereby said composition provides durable antimicrobial activity when applied to a surface.

2. The composition of claim 1, wherein said monomeric moieties provide at least 25% of the total weight of said polyurethane polymer.

3. The composition of claim 1, wherein a dye is incorporated into the molecular structure of the polyurethane polymer by covalent chemical bonding via either polymerization with other monomers or reaction with an existing polyurethane polymer, thereby preventing migration of the dye from the polymer.

4. The composition of claim 3, wherein the dye is fluorescein.

5. The composition of claim 1, wherein said monomeric moieties are selected from the group of polyoxyethylenemonoalkylmethylammonium salts.

6. The composition of claim 1, wherein said antimicrobial polymer is synthesized using step-growth polymerization.

7. The composition of claim 1, wherein said solvent consists essentially of one or more alcohols selected from the group consisting of ethanol, methanol, and isopropanol.

8. The composition of claim 1, wherein said solvent is comprised of 60-95% by weight of said alcohol.

9. The composition of claim 1, wherein said polyurethane polymer has an antimicrobial activity which does not require leaching, elution, or releasing from the surface to which the antimicrobial composition is applied.

10. The composition of claim 1, wherein said composition has a pH between 5 and 9.

11. The composition of claim 1, wherein said composition is in a form selected from the group consisting of liquid, gel, foam, and aerosol.

12. The composition of claim 1, wherein said antimicrobial composition further comprises at least one additive selected from the group consisting of a drug, an antimicrobial agent, an antiseptic agent, a thickening agent, a moisturizer, an emollient, a vitamin, a temporary dye, a permanent dye, and a UV absorber.

13. The composition of claim 12, wherein said additive is an emollient.

14. The composition of claim 13, wherein said emollient is propylene glycol, dipropylene glycol, glycerol, or a mixture thereof.

* * * * *